(12) United States Patent
Blank et al.

(10) Patent No.: US 10,722,138 B2
(45) Date of Patent: Jul. 28, 2020

(54) METHOD AND SYSTEM FOR ELECTRON PARAMAGNETIC RESONANCE

(71) Applicant: Technion Research & Development Foundation Limited, Haifa (IL)

(72) Inventors: Aharon Blank, Kfar-Vradim (IL); Periannan Kuppusamy, Hanover, NH (US); Ahmad Rizwan, Columbus, OH (US)

(73) Assignee: Technion Research & Development Foundation Limited, Haifa (IL)

( * ) Notice: Subject to any disclaimer, the term of this patent is extended or adjusted under 35 U.S.C. 154(b) by 898 days.

(21) Appl. No.: 15/318,073

(22) PCT Filed: Jun. 11, 2015

(86) PCT No.: PCT/IL2015/050596
§ 371 (c)(1),
(2) Date: Dec. 12, 2016

(87) PCT Pub. No.: WO2015/189852
PCT Pub. Date: Dec. 17, 2015

(65) Prior Publication Data
US 2017/0105651 A1  Apr. 20, 2017

Related U.S. Application Data

(60) Provisional application No. 62/011,147, filed on Jun. 12, 2014.

(51) Int. Cl.
*A61B 5/055* (2006.01)
*G01R 33/38* (2006.01)
(Continued)

(52) U.S. Cl.
CPC .......... *A61B 5/055* (2013.01); *A61B 5/14503* (2013.01); *A61B 5/14542* (2013.01);
(Continued)

(58) Field of Classification Search
CPC . A61B 5/055; A61B 5/14542; A61B 5/14503; A61B 5/6833; A61B 5/748;
(Continued)

(56) References Cited

U.S. PATENT DOCUMENTS 5,390,673 A   2/1995 Kikinis
5,678,548 A * 10/1997 Murugesan ............ G01R 33/60
                                                    600/413

(Continued)

FOREIGN PATENT DOCUMENTS

CN        1417572        5/2003
CN        1852678       10/2006
(Continued)

OTHER PUBLICATIONS

Translation Dated May 24, 2019 of Notification of Office Action dated Apr. 26, 2019 From the State Intellectual Property Office of the People's Republic of China Re. Application No. 201580036313.5. (21 Pages).

(Continued)

*Primary Examiner* — Dixomara Vargas

(57) ABSTRACT

Electron paramagnetic resonance (EPR) systems and methods for transcutaneous oxygen monitoring (TCOM) and subcutaneous oxygen monitoring (SCOM) are provided herein. Optionally, the EPR systems provided herein can be portable and/or handheld to facilitate EPR oximetry in clinical environments.

25 Claims, 13 Drawing Sheets
(8 of 13 Drawing Sheet(s) Filed in Color)

(51) Int. Cl.

| | |
|---|---|
| *G01R 33/383* | (2006.01) |
| *G01R 33/60* | (2006.01) |
| *A61B 5/145* | (2006.01) |
| *A61B 5/00* | (2006.01) |
| *G01R 33/28* | (2006.01) |
| *G01R 33/44* | (2006.01) |
| *G01R 33/343* | (2006.01) |

(52) U.S. Cl.
CPC ............ *A61B 5/6833* (2013.01); *A61B 5/748* (2013.01); *G01R 33/285* (2013.01); *G01R 33/383* (2013.01); *G01R 33/3808* (2013.01); *G01R 33/60* (2013.01); *A61B 2560/0406* (2013.01); *A61B 2560/0418* (2013.01); *A61B 2562/0223* (2013.01); *A61B 2562/046* (2013.01); *G01R 33/343* (2013.01); *G01R 33/448* (2013.01)

(58) Field of Classification Search
CPC .. G01R 33/3808; G01R 33/383; G01R 33/60; G01R 33/385
See application file for complete search history.

(56) References Cited

U.S. PATENT DOCUMENTS

| | | | |
|---|---|---|---|
| 5,706,805 A | | 1/1998 | Swartz et al. |
| 5,865,746 A | * | 2/1999 | Murugesan ............ G01R 33/60 600/410 |
| 6,163,154 A | | 12/2000 | Anderson et al. |
| 9,392,957 B1 | * | 7/2016 | Halpern ............... G01R 33/341 |
| 10,564,308 B1 | * | 2/2020 | Godoy .................. G01N 24/10 |
| 2004/0147833 A1 | | 7/2004 | Czipott et al. |
| 2005/0021019 A1 | | 1/2005 | Hashimshony et al. |
| 2010/0001728 A1 | | 1/2010 | Blank et al. |
| 2010/0072994 A1 | | 3/2010 | Lee et al. |
| 2012/0223705 A1 | | 9/2012 | Lowery et al. |
| 2012/0296188 A1 | | 11/2012 | Kuppusamy et al. |
| 2013/0046164 A1 | | 2/2013 | Liu et al. |
| 2013/0127466 A1 | | 5/2013 | Kuppusamy et al. |
| 2015/0185299 A1 | * | 7/2015 | Rinard ............... G01R 33/3657 324/322 |
| 2016/0324438 A1 | * | 11/2016 | Halpern ............... G01R 33/341 |

FOREIGN PATENT DOCUMENTS

| | | |
|---|---|---|
| CN | 1914500 | 2/2007 |
| WO | WO 2005/073695 | 8/2005 |

OTHER PUBLICATIONS

Notification of Office Action and Search Report dated Apr. 26, 2019 From the State Intellectual Property Office of the People's Republic of China Re. Application No. 201580036313.5. (13 Pages).
International Search Report and the Written Opinion dated Oct. 25, 2015 From the International Searching Authority Re. Application No. PCT/IL2015/050596.
Supplementary European Search Report and the European Search Opinion dated Jan. 24, 2018 From the European Patent Office Re. Application No. 15806716.5. (10 Pages).
Ahmad et al. "Theory, Instrumentation, and Applications of Electron Paramagnetic Resonance (EPR) Oximetry", Chemical Reviews, XP055441105, 110(5): 3212-3236, May 12, 2010. Sections 2.1.2, 3, 3.2, 4.1.1, 4.1.4, 5.4.1.
Sirota et al. "Pulsed Electron Spin Resonance Ex Situ Probe for Tooth Biodosimetry", Applied Magnetic Resonance, XP055441109, 44(6): 671-689, Published Online Jan. 24, 2013. Sections 1, 2.3, Fig. 1.
Twig et al. "Sensitive Surface Loop-Gap Microresonators for Electron Spin Resonance", Review of Scientific Instruments, XP012145495, 81(10: 104703-1-104703-11, Published Online Oct. 21, 2010. Chap. III.
Wolfson et al. "A Hand-Held EPR Scanner for Transcutaneous Oximetry", Proceedings of the SPIE: Progress in Biomedical Optics and Imaging, XP060051433, 9417: 941706-1-941706-9, Mar. 19, 2015.
Wolfson et al. "A Miniature Electron Spin Resonance Probehead for Transcutaneous Oxygen Monitoring", Applied Magnetic Resonance, XP055441319, 45(10): 955-967, Published Online Sep. 21, 2014.

\* cited by examiner

METHOD AND SYSTEM FOR ELECTRON PARAMAGNETIC RESONANCE

RELATED APPLICATIONS

This application is a National Phase of PCT Patent Application No. PCT/IL2015/050596 having International filing date of Jun. 11, 2015, which claims the benefit of priority under 35 USC § 119(e) of U.S. Provisional Patent Application No. 62/011,147 filed on Jun. 12, 2014. The contents of the above applications are all incorporated by reference as if fully set forth herein in their entirety.

STATEMENT REGARDING FEDERALLY FUNDED RESEARCH

This invention was made with government support under Grant No. 1 R21 EB016189 01 from the National Institutes of Health (NIH)/NIBIB. The government may have certain rights in the invention.

FIELD AND BACKGROUND OF THE INVENTION

The present invention, in some embodiments thereof, relates to electron paramagnetic resonance and, more particularly, but not exclusively, to a electron paramagnetic resonance system useful for oxygen monitoring.

Any imbalance in tissue oxygen levels may affect metabolic homeostasis and lead to pathophysiological conditions. For instance, the role of hypoxia in cancer treatment and wound healing has been well documented. There are only two technologies in mainstream clinical use that directly measure oxygenation status: arterial catheters and transcutaneous oxygen monitoring (TCOM) using electrodes. These technologies are primarily used for critical-care monitoring.

Arterial catheters are most commonly placed and maintained within the radial artery and measure oxygen levels in the blood that indicate systemic oxygen availability but not actual tissue oxygenation. This is a very important distinction because adequate oxygenation of the blood is not always accompanied by tissue uptake of oxygen. The invasive nature of monitoring oxygenation levels with a catheter in a blood vessel is also accompanied by significant risks to the patient, e.g., direct access of bacteria from the external environment to the patient's blood stream along the surface of the catheter, occlusion of the artery by the catheter resulting in critical ischemia to the hand, etc.

Electrode-based TCOM is the only non-invasive, clinically-approved methodology that estimates tissue oxygenation by measuring the diffusion of extracellular oxygen through the skin. The method is quantitative and is the only method that measures oxygen delivery to an end organ (in this case, the skin). It has been used to monitor oxygen levels in the skin, especially for premature infants, but also for adults in the intensive care setting. It is used to determine the healing capacity of wounds, but is only used in about 2% of chronic wound cases. For this procedure, the patient's skin must be shaved and the top layer removed. Electrodes are then clamped to the patient's skin via fixation rings and heated to 100 degrees Fahrenheit. In some cases this process can cause first-degree burns on the patient, especially infants. After heating, the user performs oxygen measurement of the underlying tissue. The entire process can last from 45 to 90 minutes. These drawbacks, along with a high rate of user error (some experts estimate error to be as high as 60% due to procedural complexity), leads to a low usage rate of this technology.

Measuring oxygen concentration (pO2) by electron paramagnetic resonance (EPR) involves the use of an exogenous probe including paramagnetic material in either solid or soluble form. The changes in the relaxation times (T2) of the EPR probe are caused by the interaction of two paramagnetic species molecular oxygen and the EPR probe. These reversible oxygen-induced changes in the relaxation times are used to quantify pO2. EPR oximetry offers unique advantages over other existing oximetry methods, including high sensitivity to pO2 and high functional specificity. Unlike BOLD MRI and pulse oximetry, which measure blood oxygen saturation, EPR oximetry measures the tissue oxygen concentration directly. In the last fifteen years, several sensitive, nontoxic, particulate oximetry probes have been developed. The long-term stability of some of these probes in tissue has also been established. More importantly, particulate-based EPR oximetry is "minimally invasive" because the particulate probe is implanted only one time, and the subsequent measurements are carried out without any invasive procedure.

However, existing hardware system limitations make the use of EPR oximetry for clinical purposes less ideal. As most conventional EPR systems are large, bulky units with restrictive spacing between the magnet poles, refinements in EPR system hardware would make this technology more appealing from a clinical standpoint. The movement towards smaller, portable EPR systems would be of substantial benefit to both the end user (e.g., clinicians, clinical technicians, etc.) and the patients for whom such a system would be intended. As a smaller, portable system, the EPR oximetry system would have the capability to be transported from room to room, rather than have the patient brought to a separate location. In critical-care settings, this would be most useful, as moving the patient is often not an option.

SUMMARY OF THE INVENTION

Electron paramagnetic resonance (EPR) systems and methods for transcutaneous oxygen monitoring (TCOM) and subcutaneous oxygen monitoring (SCOM) are provided herein. Optionally, the EPR systems provided herein can be portable and/or handheld to facilitate EPR oximetry in clinical environments.

An example system for detecting an electron paramagnetic resonance (EPR) signal from an oxygen-sensitive EPR probe material can include a radio frequency (RF) source, a housing containing a magnetic assembly, a resonator assembly and a coupling loop and a spectrometer. The housing can have a distal end positionable proximal to the EPR probe. Additionally, the magnet assembly can be configured to apply a magnetic field to a region-of-interest including the EPR probe.

The resonator assembly can be in operative communication with the RF source through the coupling loop and can be configured to resonate at a predetermined radio frequency. The spectrometer can be in operative communication with the resonator assembly through the coupling loop and configured to receive a signal from the coupling loop and process the received signal to measure EPR resonance of the EPR probe.

Additionally, the EPR probe can be an oxygen-sensitive EPR material embedded in an oxygen-permeable polymer. Optionally, the EPR probe can be adhered to a surface of a tissue of a subject. The spectrometer can be configured to obtain data corresponding to a transcutaneous oxygen concentration of the tissue from the signal. In addition, the distal end of the housing can optionally include an indentation for accommodating a portion of the EPR probe. Alternatively or additionally, the EPR probe can be implanted in a tissue of a subject. The spectrometer can be configured to obtain data corresponding to a subcutaneous oxygen concentration of the tissue from the signal.

The housing can optionally be a handheld wand. Additionally, the region-of-interest can be located at least partially external to the handheld wand. Alternatively or additionally, the region-of-interest can be located entirely external to the handheld wand. For example, the region-of-interest can be located approximately 3 mm from the handheld wand, as measured along the axial direction. Optionally, a maximum size of the region-of-interest can be approximately 0.5 mm×0.5 mm×0.5 mm.

Alternatively or additionally, the magnetic assembly can include a plurality of magnets, and the magnets can be arranged around the resonator assembly. For example, the magnets can optionally be arranged in a ring around the resonator assembly. The magnet assembly can be configured to generate a substantially uniform magnetic field in the region-of-interest. For example, the substantially uniform magnetic field can optionally have a field inhomogeneity of approximately 1000 ppm or less across the entire region-of-interest.

Additionally, the predetermined radio frequency can be substantially greater than 250 MHz. For example, the predetermined radio frequency can be in a range between approximately 2.0 GHz and 6.2 GHz. Optionally, the substantially uniform magnetic field can have a strength of approximately 60-150 mT, or 60-120 mT or 80-120 mT. Alternatively, the substantially uniform magnetic field can have a strength of approximately 200-220 mT.

Optionally, the resonator assembly can be a loop-gap resonator. Alternatively or additionally, the RF source can generate RF pulses.

An example wand for use with a system for detecting an electron paramagnetic resonance (EPR) signal from an oxygen-sensitive EPR probe material can include a housing containing a magnetic assembly and a resonator assembly. The housing can have a distal end positionable proximal to the EPR probe. Additionally, the magnet assembly can be configured to apply a magnetic field to a region-of-interest including the EPR probe. The resonator assembly can be configured to resonate at a predetermined radio frequency.

The housing can optionally be a handheld wand. Additionally, the region-of-interest can be located at least partially external to the handheld wand. Alternatively or additionally, the region-of-interest can be located entirely external to the handheld wand. For example, the region-of-interest can be located approximately 3 mm from the handheld wand. Optionally, a maximum size of the region-of-interest is approximately 0.5 mm×0.5 mm×0.5 mm. Additionally, the housing can include a coupling loop for operatively connecting the wand to at least one of a radio frequency source and a spectrometer.

An example magnet and resonator assembly housing for use with a system for detecting an electron paramagnetic resonance (EPR) signal from an oxygen-sensitive EPR probe material can include a plurality of permanent magnets configured to generate a uniform magnetic field in a region-of-interest including the EPR probe and a resonator configured to resonate at a specific radio frequency. Additionally, the permanent magnets can be arranged around the resonator. A distal end of the housing can be positionable proximal to the EPR probe.

Optionally, the substantially uniform magnetic field can have a strength of approximately 60-150 mT, or 60-120 mT or 80-120 mT with a field inhomogeneity of approximately 1000 ppm or less across the entire region-of-interest. The permanent magnets can optionally be arranged around the resonator in a closed-loop shape. For example, the closed-loop shape can optionally be a ring. Additionally, an outer dimension of the closed-loop shape can optionally be approximately 30 mm or approximately 20 mm. Alternatively or additionally, an outer dimension of the resonator can optionally be about 8 mm or about 13 mm. Each of the permanent magnets can optionally be a hexahedron. Additionally, each of the permanent magnets can optionally be an approximately 4 mm×4 mm×8 mm hexahedron.

Optionally, the substantially uniform magnetic field can have a strength of approximately 200-220 mT with a field inhomogeneity of approximately 1000 ppm or less across the entire region-of-interest. Additionally, the permanent magnets can be arranged around the resonator. For example, the resonator can be arranged in a space between at least two permanent magnets. Additionally, an outer dimension of the permanent magnets can be approximately 70 mm. Alternatively or additionally, an outer dimension of the resonator can optionally be about 8 mm or about 13 mm.

Alternatively or additionally, each of the permanent magnets can be formed from samarium-cobalt.

Optionally, the resonator can be a loop-gap resonator. The predetermined radio frequency can be substantially greater than 250 MHz. For example, the predetermined radio frequency can be in a range between approximately 2.0 GHz and 6.2 GHz.

Alternatively or additionally, the magnet and resonator assembly housing can include a coupling loop arranged adjacent to the resonator and configured to operatively connect the resonator to at least one of a radio frequency source and a spectrometer.

An example method for detecting an electron paramagnetic resonance (EPR) signal from an oxygen-sensitive EPR probe material using a wand and a spectrometer is described below. The wand can include a housing containing a magnetic assembly, a resonator assembly and a coupling loop. Additionally, the magnet assembly can be configured to apply a magnetic field to a region-of-interest including the EPR probe. The resonator assembly can be configured to resonate at a predetermined radio frequency. The method can include detecting a signal in the region-of-interest when a distal end of the housing of the wand is positioned proximal to the EPR probe, communicating the detected signal through the coupling loop to the spectrometer and processing the received signal to measure EPR resonance of the EPR probe.

Additionally, the EPR probe can be an oxygen-sensitive EPR material embedded in an oxygen-permeable polymer. Optionally, the EPR probe can be adhered to a surface of a tissue of a subject. The method can further include obtaining data corresponding to a transcutaneous oxygen concentration of the tissue from the signal. Alternatively or additionally, the EPR probe can be implanted in a tissue of a subject. The method can further include obtaining data corresponding to a subcutaneous oxygen concentration of the tissue from the signal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a block diagram illustrating a system for detecting an EPR signal from an oxygen-sensitive EPR probe material, according to some embodiments of the present invention;

FIG. 1B is a diagram illustrating a region-of-interest according to some embodiments of the present invention;

FIG. 2A illustrates an example magnet assembly according to some embodiments of the present invention;

FIG. 2B illustrates an example resonator assembly and coupling loop according to some embodiments of the present invention;

FIG. 2C is a perspective view illustrating the magnet assembly and resonator assembly shown in FIGS. 2A-2B;

FIG. 2D illustrates a wand containing the magnet assembly and resonator assembly shown in FIG. 2C;

FIG. 3A illustrates another example magnet assembly and resonator assembly according to some embodiments of the present invention;

FIG. 3B is a graph illustrating the magnetic field of the magnet assembly shown in FIG. 3A;

FIG. 4 illustrates an example oxygen-sensitive EPR probe material;

FIG. 5A illustrates example oxygen-sensitive EPR probe materials;

FIGS. 5B and 5C show data related to the oxygen-sensitive EPR probe materials of FIG. 5A;

Figure 6A:
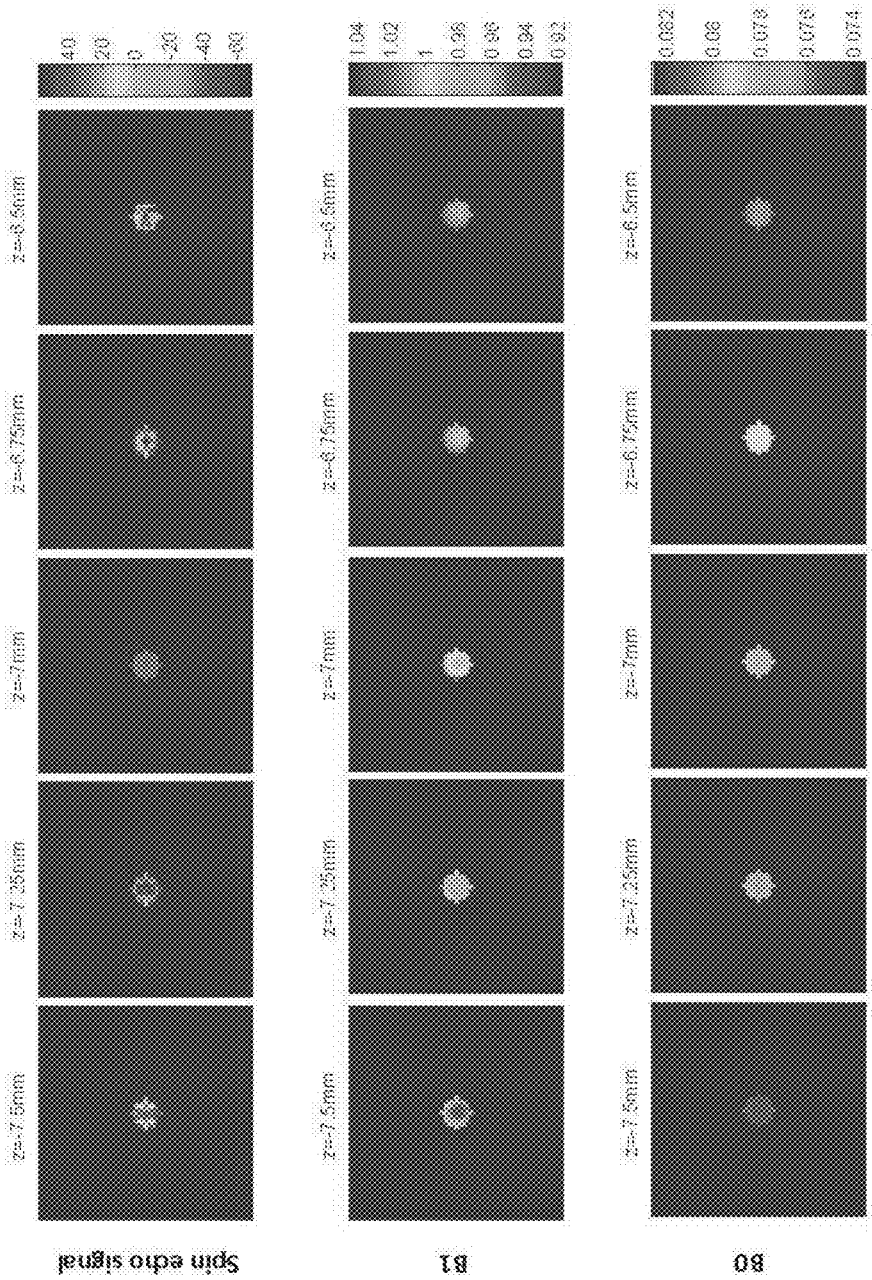
Figure 6B:
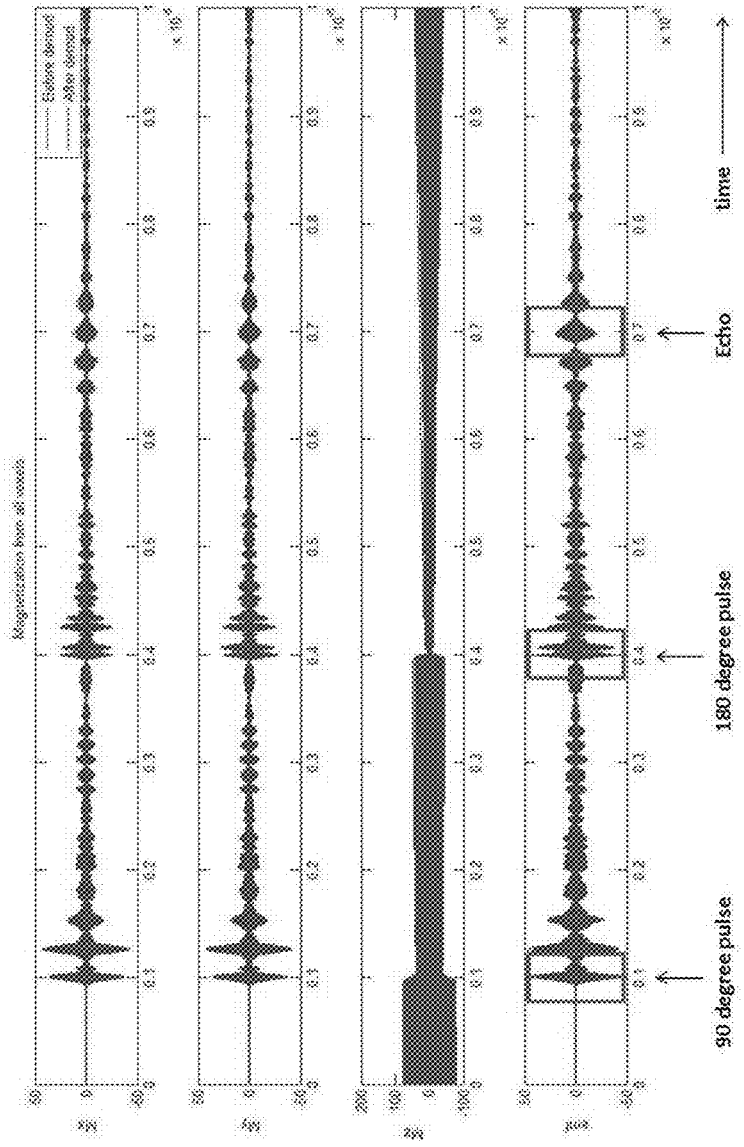
Figure 7:
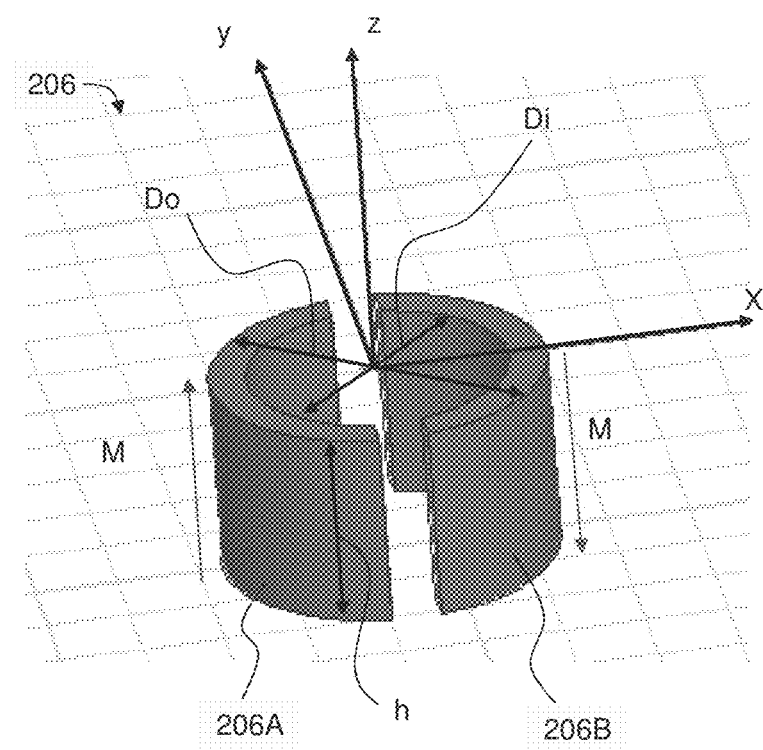
Figure 8:
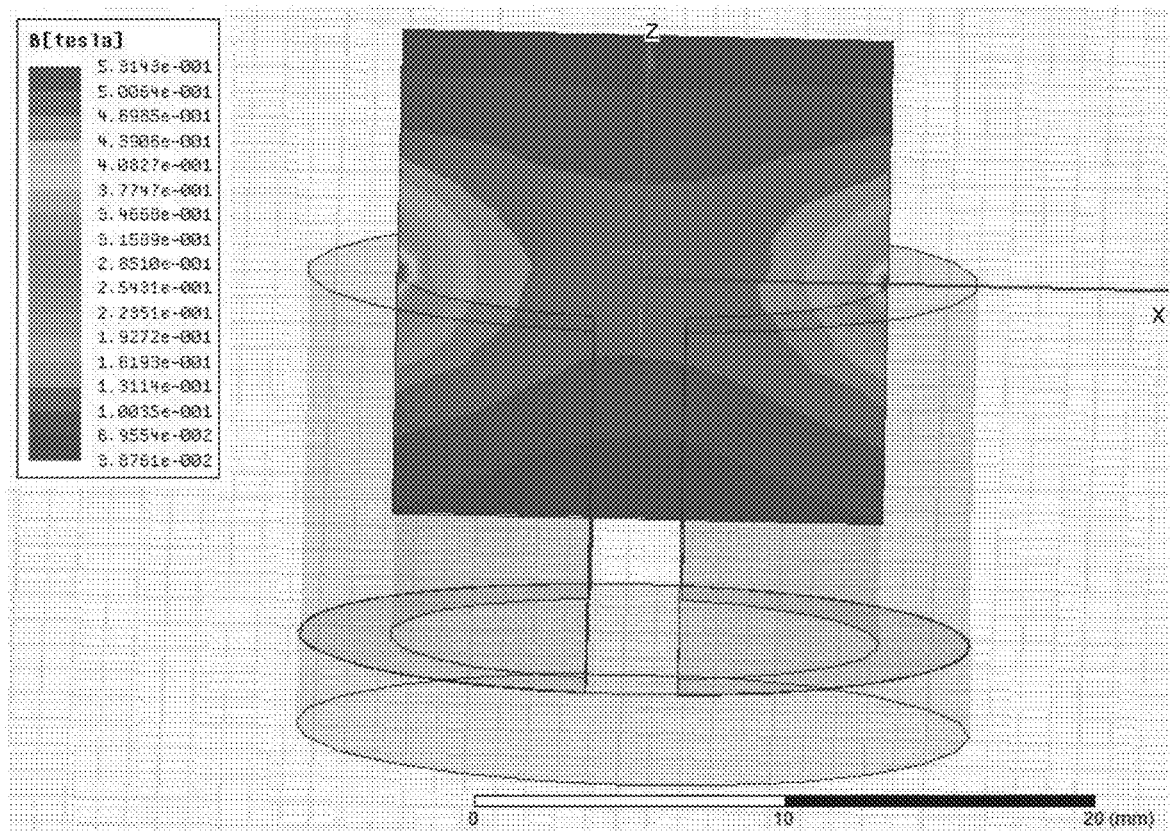
Figure 9A:
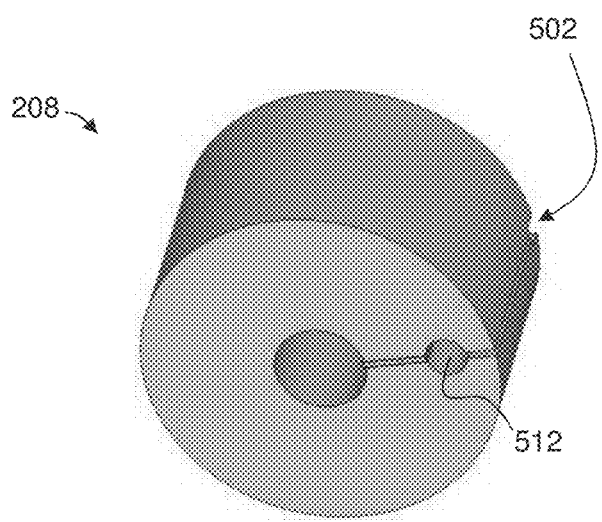
Figure 9B:
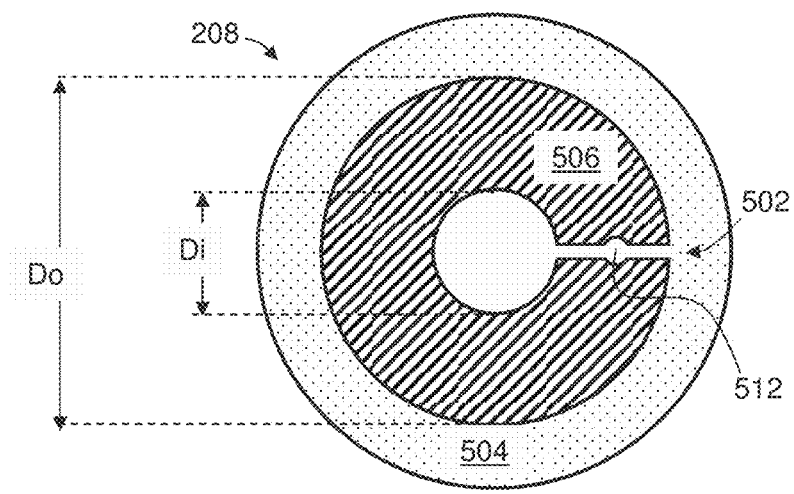
Figure 10:
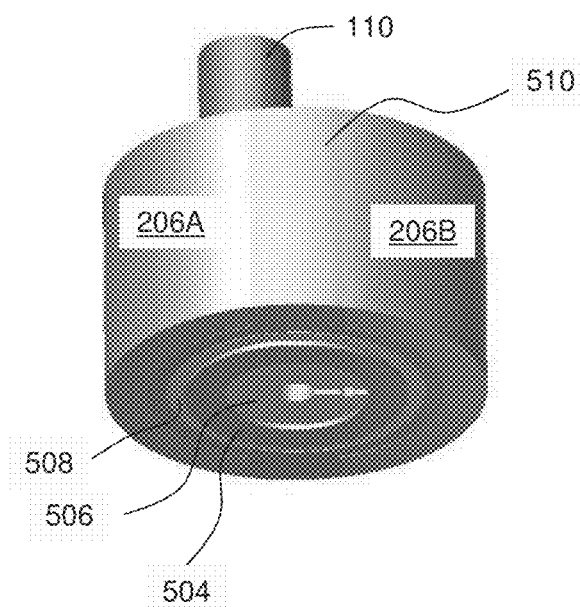
Figure 11:
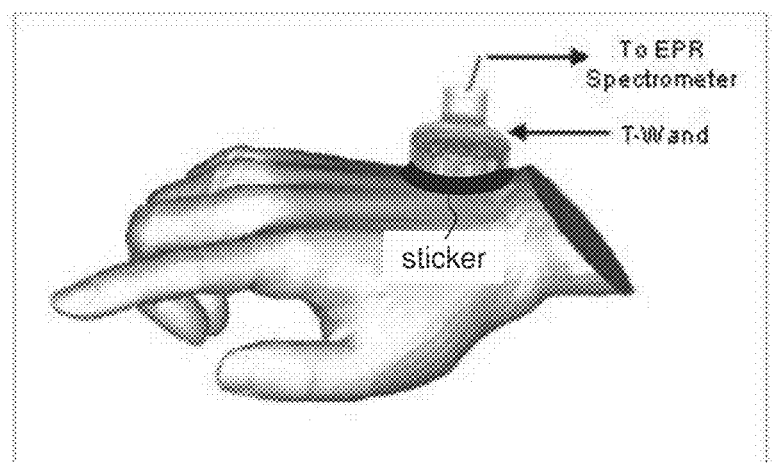

FIGS. 6A and 6B illustrate the results of spin echo stimulations on the magnet and resonator assemblies of FIGS. 2A-2D;

FIG. 7 illustrates a magnet assembly having two parts each shaped as a half of a cylinder, according to some embodiments of the present invention;

FIG. 8 shows the magnetic field contour formed by the magnet assembly of FIG. 7, as obtained by computer simulations performed according to some embodiments of the present invention;

FIGS. 9A and 9B illustrate a perspective view (FIG. 9A) and a cross-sectional view (FIG. 9B) of another example of a resonator assembly according to some embodiments of the present invention;

FIG. 10 illustrates a perspective view showing the arrangement of the magnet assembly of FIG. 7 and the resonator assembly of FIGS. 9A and 9B once assembled together according to various exemplary embodiments of the present invention; and FIG. 11 illustrates a wand containing a magnet assembly, a resonator assembly and a skin attachable sticker, according to some embodiments of the present invention.

DESCRIPTION OF SPECIFIC EMBODIMENTS OF THE INVENTION

The present invention, in some embodiments thereof, relates to electron paramagnetic resonance and, more particularly, but not exclusively, to a electron paramagnetic resonance system useful for oxygen monitoring.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

While implementations will be described for providing EPR systems and methods for TCOM and SCOM, it will become evident to those skilled in the art that the implementations are not limited thereto.

The ability to monitor transcutaneous and subcutaneous oxygen levels carries enormous clinical significance. For example, wound-healing assessment, hyperbaric therapy, amputation-level determination, neonatal intensive care, and perfusion-status determination during surgery or transplantation can benefit immensely from development of oximetry techniques that are fast, accurate and can be used in clinical settings. Unfortunately, presently available in vivo oximetry methods are not ideally suitable for clinical applications. An electron paramagnetic resonance (EPR) system capable of transcutaneous oxygen monitoring (TCOM) as well as subcutaneous oxygen monitoring (SCOM) is provided herein. The EPR system can optionally be used in clinical settings.

Over the past couple of decades, EPR oximetry techniques have been continually refined to collect direct, repetitive, minimally invasive, and accurate measurements of oxygen levels in biological samples. As opposed to deep tissue oximetry where penetration depth can be a limiting factor, EPR is well-suited for transcutaneous and subcutaneous measurements. However, current EPR instruments are not designed for clinical settings, and their bulky, non-portable design and limited sample space make them an unattractive choice for clinical applications.

Conventionally, EPR systems invariably consist of a Helmholtz pair or a pair of permanent magnets. The design is not only bulky but the resulting geometry is unfit to accommodate large samples. Additionally, conventional in vivo EPR systems operate at relatively low frequencies, mainly for the purpose of overcoming problems of microwave penetration into tissue of a subject.

It was found by the present inventor that EPR signal can be used for measuring tissue oxygen levels. This can be done by attaching to a skin part of a subject a sticker having an oxygen-sensitive EPR probe material, measuring an EPR signal from the sticker a predetermined time-period following the attachment, and analyzing the EPR signal to determine oxygen levels at the skin part.

As used herein, "oxygen-sensing EPR material" and "oxygen-sensing EPR probe material" interchangeably refer to a material that exhibits an EPR signal peak, and preferably a signal peak, that varies with changes in concentration of molecular oxygen nearby or in contact with the material.

Representative examples of oxygen-sensing EPR materials suitable for the present embodiments are provided below.

The sticker can have any size compatible with the skin part to which it is attached. Preferably, but not necessarily, the sticker is sufficiently small to allow attaching it also to small organs (e.g., palms, fingers, ears, etc.). In these embodiments the largest diameter of the sticker is preferably less than 8 cm or less than 7 cm or less than 6 cm or less than 5 cm or less than 4 cm or less than 3 cm, e.g., about 2 cm or less.

The EPR signal can be measured by placing on the sticker (e.g., in contact relation) an ex situ EPR device having a static magnetic field generator and a resonator. Preferably, during at least a portion (e.g., at least 50% or at least 50% or at least 60% or at least 70% or at least 80% or at least 90% or at least 95% or at least 99%) of the predetermined time-period at which the sticker is attached to the skin part, no electrical or magnetic or electromagnetic signals are collected from the sticker. Only at the end of the predetermined time-period, the ex situ EPR device is placed on the sticker for collecting the EPR signal. The duration of the measurement is preferably considerably shorter than the predetermined time-period at which the sticker is attached to the skin part. Thus, denoting the predetermined time-period by $\Delta T$ and the duration of the measurement by $\Delta T_{EPR}$, according to some embodiments of the present invention, the ratio R defined as $R=\Delta T/\Delta T_{EPR}$, is at least 100 or at least 200 or at least 400 or at least 800 or at least 1600 or at least 3200.

In some embodiments of the present invention $\Delta T$ is at least 60 minutes or at least 60 minutes or at least 90 minutes or at least 120 minutes or at least 150 minutes or at least 180 minutes or at least 210 minutes or at least 240 minutes or at least 270 minutes or at least 300 minutes or more.

In some embodiments of the present invention $\Delta T_{EPR}$ is at most 60 seconds or at most 50 seconds or at most 40 seconds or at most 30 seconds or at most 20 seconds or at most 10 seconds or at most 5 seconds or less.

The analysis of the EPR signal is preferably by means of an EPR spectrometer configured for providing a signal indicative of changes in the EPR relaxation times of the oxygen-sensitive EPR probe material, and a data processor configured for correlating the EPR relaxation times to oxygen levels by means of a correlation procedure that may employ a lookup table, a mathematical function or the like.

The technique of the present embodiments enjoys many advantages over conventional TCOM systems. One advantage is that there is no need to clamp and seal the probe material. Another advantage is that there is no need to wait many minutes for the oxygen to equilibrate with the TCOM solution. Another advantage is that, unlike conventional TCOM systems, the sticker of the present embodiments can be placed on small organs (e.g., a figure). An additional advantage is that more than one (e.g., three or more, or four or more) stickers can be respectively attached to more than one spatially separated skin parts, wherein all or a portion of the stickers remain on the respective skin parts at least a portion of the predetermined time-period, and wherein the EPR signal is measured from each of the stickers.

For TCOM and SCOM applications, where penetration depth is not a limiting factor and the oxygen-sensitive EPR probe material can be positioned in close vicinity to a wand, the wand can include a relatively small magnet and still operate at a relatively high frequency (e.g., 2.0 GHz to 6.2 GHz) for better SNR. As discussed below, EPR systems for TCOM or SCOM can optionally use a pulsed EPR spectrometer in conjunction with a handheld wand. When the wand is positioned in close vicinity to an oxygen-sensitive EPR probe material, the spectrometer is capable of detecting/measuring changes in the relaxation times (T2) of the oxygen-sensitive EPR probe (e.g., an EPR signal) caused by the interaction of two paramagnetic species, which can be used to quantify oxygen concentration (pO2), for example, oxygen concentration of a tissue of a subject. This general approach is termed "mobile" magnetic resonance or "ex situ" magnetic resonance.

Figure 1A:
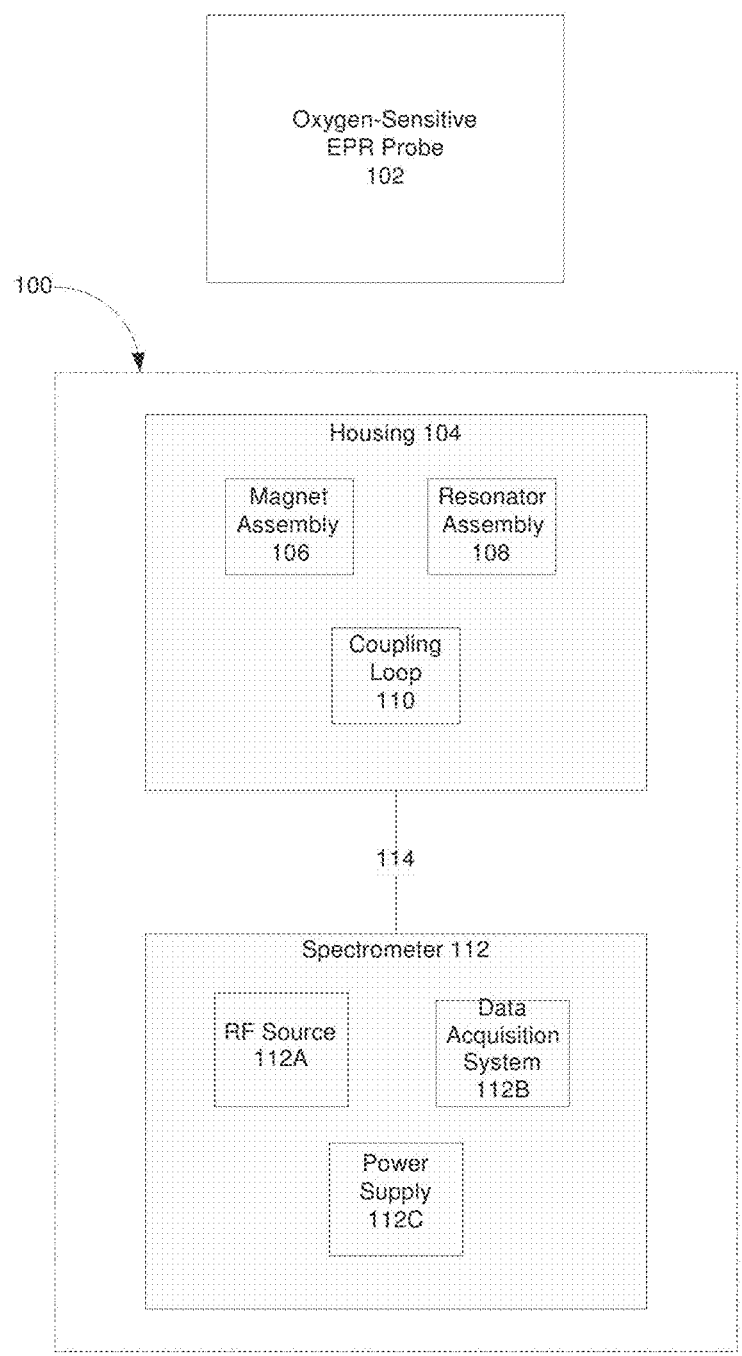

Referring now to FIG. 1A, a block diagram of a system 100 for detecting an EPR signal from an oxygen-sensitive EPR probe material 102 is shown. The system 100 can include a housing 104 that contains a magnet assembly 106, a resonator assembly 108 and a coupling loop 110. Optionally, the housing 104 can be a portable (or handheld) wand. The magnet assembly 106 can be configured to generate (and apply) a magnetic field to a region-of-interest including the EPR probe 102. The resonator assembly 108 can be configured to resonate at a predetermined radio frequency. The system 100 can also include a spectrometer 112. Additionally, the spectrometer 112 can optionally include a radio frequency (RF) source 112A, data acquisition system 112B, and power supply 112C. The RF source 112A can be configured to generate and supply RF energy (e.g., microwave energy) to the resonator assembly 108, for example. Alternatively, the RF source 112A can optionally be provided separately from the spectrometer 112. The coupling loop 110 can be configured to electromagnetically couple resonator assembly 108 to the spectrometer 112 (and/or the RF source 112A). Additionally, a communication link 114 can be used to connect the housing 104 and the spectrometer 112. This disclosure contemplates the communication link 114 is any suitable communication link. For example, a communication link may be implemented by any medium that facilitates data exchange between the housing 104 and the spectrometer 112 including, but not limited to, wired, wireless and optical links.

Spectrometers are well known in the art and are therefore not discussed in further detail below. Optionally, the spectrometer 112 can be a broadband pulsed EPR spectrometer (e.g., operating in the 2.0 GHz-6.2 GHz range). For example, the spectrometer 112 can be configured to measure the transverse (or spin-spin) relaxation times (T2) of the oxygen-sensitive EPR probe material 102. Measurement of oxygen concentration (pO2) by EPR involves the use of an exogenous probe including paramagnetic material in either solid or soluble form (e.g., the oxygen-sensitive EPR probe material 102). Changes in the relaxation times (T2) of the oxygen-sensitive EPR probe material 102 are caused by the interaction of two paramagnetic species—molecular oxygen and the paramagnetic material of the oxygen-sensitive EPR probe material 102. These reversible oxygen-induced changes in the relaxation times (T2) can be used to quantify oxygen concentration (pO2).

EPR systems for TCOM or SCOM can be designed for pulsed operation, which makes the EPR systems less susceptible to mechanical motions as compared to continuous wave (CW) designs. Additionally, by using relatively small resonators, the use of high-power amplifiers can be eliminated and all measurements can be completed with low-power, inexpensive, solid-state sources. Additionally, because of the availability of high efficiency of resonators, a power of about 4 W can be sufficient to provide adequate excitation bandwidth.

Figure 1B:
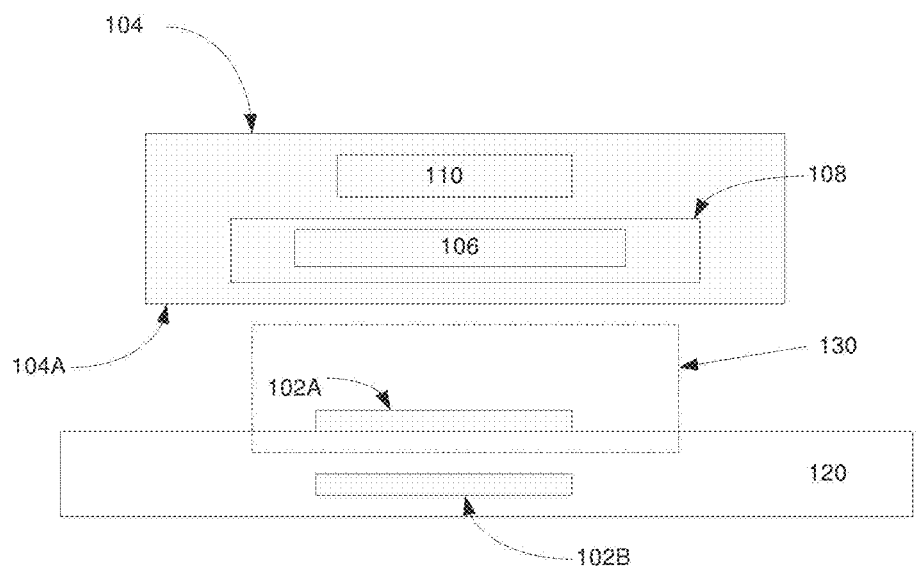

As discussed above with regard to FIG. 1A, the housing 104 can contain a magnet assembly 106, a resonator assembly 108 and a coupling loop 110. In other words, the housing 104 is the device or unit that holds/contains the magnet assembly 106, the resonator assembly 108 and the coupling loop 110. Optionally, the housing 104 can be a portable or handheld wand. When performing TCOM or SCOM, the housing 104 can be positioned in close vicinity to the oxygen-sensitive EPR probe material 102A, 102B, which is adhered to or embedded in tissue 120 of a subject as shown in FIG. 1B. For example, a distal end of the housing 104A can be positioned in close vicinity to the tissue 120, e.g., proximal to the oxygen-sensitive EPR probe material 102A, 102B that is adhered to or embedded in the tissue.

Additionally, the magnet assembly 106 can be configured to generate a magnetic field to a region-of-interest 130 including the oxygen-sensitive EPR probe material 102A. In other words, the oxygen-sensitive probe 102A can be located within the region-of-interest 130. Optionally, the magnet assembly 106 can be configured to generate a substantially uniform magnetic field across the entire region-of-interest 130. For example, the substantially uniform magnetic field can optionally have a field inhomogeneity of approximately 1000 ppm or less across the entire region-of-interest 130. Alternatively or additionally, the field inhomogeneity can be approximately 900-1000 ppm, 800-900 ppm, 700-800 ppm, 600-700 ppm, 500-600 ppm, 400-500 ppm, 300-400 ppm, 200-300 ppm, 100-200 ppm or less than 100 ppm across the entire region-of-interest 130. Optionally, the region-of-interest 130 can be an approximately 0.5 mm×0.5 mm×0.5 mm region. For TCOM, the oxygen-sensitive EPR probe material 102A can be adhered to a surface of a tissue 120 of a subject, and the spectrometer can be configured to obtain data corresponding to a transcutaneous oxygen concentration of the tissue from the signal. The region-of-interest 130 can reside in proximity to a surface of the tissue 120 underneath the housing 104. Additionally, the region-of-interest 130 can be located at least partially external to the housing 104. Alternatively or additionally, the region-of-interest 130 can be located entirely external to the housing 104. As discussed above, conventional EPR systems typically include a Helmholtz pair or a pair of permanent magnets. Additionally, the specimen being measured (e.g., an oxygen-sensitive EPR probe material) is placed in the area or volume between the Helmholtz pair or pair of permanent magnets in conventional EPR systems. In other words, the region-of-interest would be in the area or volume between the Helmholtz pair or pair of permanent magnets. In contrast, as shown in FIG. 1B, the region of interest 130 is located at least partially external to the housing 140 and is not located in the area or volume between any of the magnets. For SCOM, the oxygen-sensitive EPR probe material 102B can be implanted in a tissue 120 of a subject, and the spectrometer can be configured to obtain data corresponding to a subcutaneous oxygen concentration of the tissue from the signal. For example, the oxygen-sensitive EPR probe material 102B can be implanted approximately 3 mm below a surface of the tissue 120. The region-of-interest 130 can reside at least partially below a surface of the tissue 120 underneath the housing 104. Additionally, the region-of-interest 130 can be located entirely external to the housing 104. For example, the region-of-interest 130 can be located approximately 3 mm from the housing 104, as measured along the axial direction of magnet assembly 106.

Magnet assemblies can be designed for TCOM and SCOM as provided below. For example, a compact magnet assembly can be provided with permanent magnets, for example, using commercially-available, temperature-compensated samarium-cobalt (SmCo), which has a temperature stability of about 10 ppm/° C. The dimensions of the magnet assembly are determined by the size of the region-of-interest, field strength and the level of homogeneity within the region-of-interest. The homogeneity requirements are less stringent and can be achieved using a compact magnet assembly because the region-of-interest is relatively small (e.g., 0.5 mm×0.5 mm×0.5 mm) and in close proximity (for example, at about 3 mm as measured along the axial direction) to the magnet assembly.

Figure 2A:
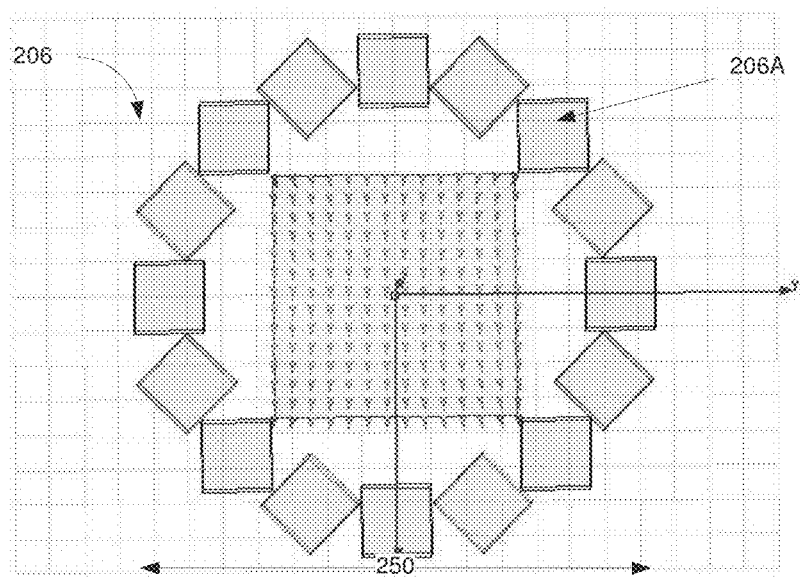
Figure 2B:
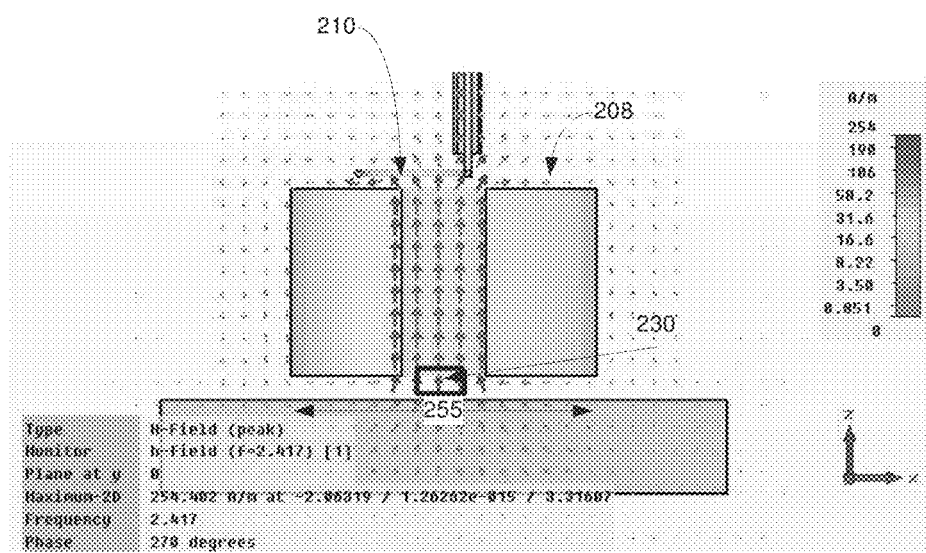
Figure 2C:
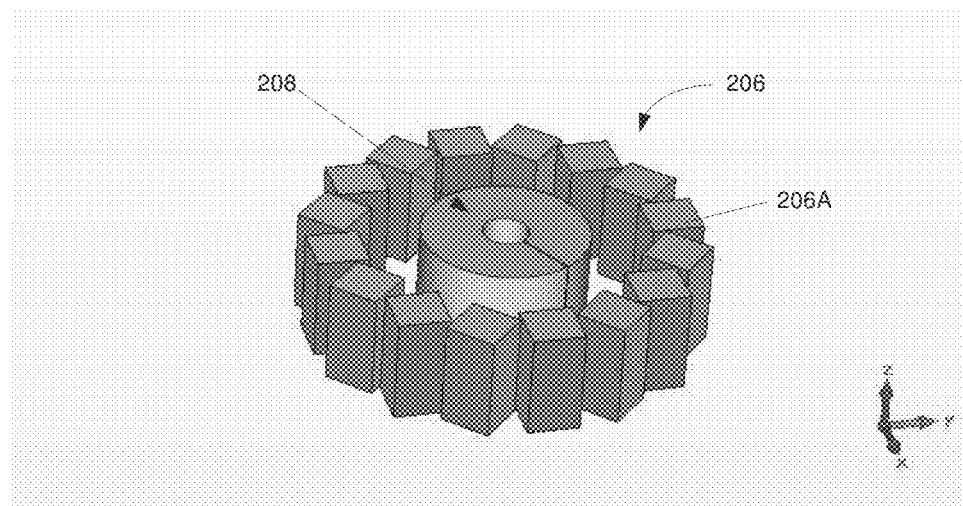

Referring now to FIGS. 2A-2C, example magnet and resonator assemblies are shown. A magnet assembly 206 can include a plurality of magnets 206A. Magnet assembly 206 can optionally be used in a TCOM wand, for example. Each of the magnets 206A can optionally be a permanent magnet such as a permanent magnet formed from SmCo. Alternatively or additionally, each of the magnets 206A can optionally be a hexahedron. For example, each of the magnets 206A can optionally be an approximately 4 mm×4 mm×8 mm hexahedron. Additionally, increased flexibility in achieving and adjusting the magnetic field to the desired homogeneity and/or strength is obtained by providing relatively small magnets 206A. Optionally, the magnets 206A can be arranged around the resonator assembly 208. For example, the magnets 206A can optionally be arranged around the resonator assembly 208 in a closed-loop shape. For example, the closed-loop shape can optionally be a ring. When the magnets 206A are arranged in a ring-shape, a magnetic field with sufficient uniformity and strength can be produced. This disclosure contemplates that the closed-loop shape is not limited to a ring and can optionally be any closed-loop shape such as a circle, an oval or a polygon. As discussed above, the magnet assembly 206 can be configured to generate a substantially uniform magnetic field in the region-of-interest 230, for example, having a field inhomogeneity of approximately 1000 ppm or less across the entire region-of-interest 230. Alternatively or additionally, the field inhomogeneity can be approximately 900-1000 ppm, 800-900 ppm, 700-800 ppm, 600-700 ppm, 500-600 ppm, 400-500 ppm, 300-400 ppm, 200-300 ppm, 100-200 ppm or less than 100 ppm across the entire region-of-interest 230.

The region-of-interest 230 can be located approximately 3 mm from the magnet assembly 206, as measured along the axial direction of the magnet assembly 206. Optionally, a maximum size of the region-of-interest 230 can be approximately 0.5 mm×0.5 mm×0.5 mm.

Optionally, the substantially uniform magnetic field can have a strength in the range of approximately 60-150 mT, or 60-120 mT or 80-120 mT, corresponding to frequency range 2.0-2.5 GHz, across the entire region-of-interest 230. For example, the substantially uniform magnetic field can optionally have a strength of about 86 mT or about 90 mT or about 100 mT, corresponding to a frequency of about 2.4 GHz, across the entire region-of-interest 230. In addition, an outer dimension 250 of the magnet assembly 206 (e.g., an outer dimension of the closed-loop shape) can optionally be from about 15 mm to about 40 mm, or from about 15 mm to about 25 mm, or from about 25 mm to about 35 mm, e.g., about 20 mm or about 30 mm.

Each of the magnets 206A can optionally be rotated relative to adjacent magnets 206A, as shown in FIGS. 2A and 2C.

The resonator assembly 208 can be a loop-gap resonator assembly and can reside inside the magnet assembly 206. The loop-gap resonator assembly 208 can have a hollowed and generally cylindrical shape having a longitudinal gap along its length. The axial length, inner diameter, outer diameter and the width and number of longitudinal gaps may be selected to provide the desired frequency, quality factor and filling factor.

The outer diameter of resonator assembly 208 is less than the inner diameter of magnet assembly 206. The outer diameter of resonator assembly 208 is preferably from about 6 mm to about 20 mm, or from about 6 mm to about 10 mm, or from about 11 mm to about 15 mm. In some embodiments of the present invention the outer diameter is about 8 mm and in some embodiments of the present invention is about 13 mm. The inner diameter of resonator assembly 208 is less than its outer diameter and can be from about 1 mm to about 5 mm, or from about 1.5 mm to about 2.5 mm, or from about 3 mm to about 4 mm. In some embodiments of the present invention the inner diameter is about 2 mm and in some embodiments of the present invention is about 3.6 mm.

The axial length of resonator assembly 208 can be from about 6 mm to about 10 mm, e.g., about 8 mm. The width of the gap can be from about 60 μm to about 140 μm, or from about 80 μm to about 120 μm, or from about 90 μm to about 110 μm, e.g., about 100 μm.

In some embodiments of the present invention resonator assembly 208 is supported from the outside by a resonator support element (not shown, see 504 in FIG. 9B) which is preferably formed from an electrically insulating material. Any material having sufficiently low dielectric loss and sufficiently high dimensional stability can be used as a resonator support element. In a preferred embodiment, a polystyrene material such as that sold under the trademark "Rexolite®" is used. The resonator support element can be in the form of a circular cylindrical retainer which encircles the resonator assembly 208 and retains its radial and axial position by frictional engagement. The dimensions of the resonator support element are selected according to the outer diameter of assembly 208.

A representative example of a loop-gap resonator assembly suitable for the present embodiments is provided in the Examples section that follows.

Figure 2D:
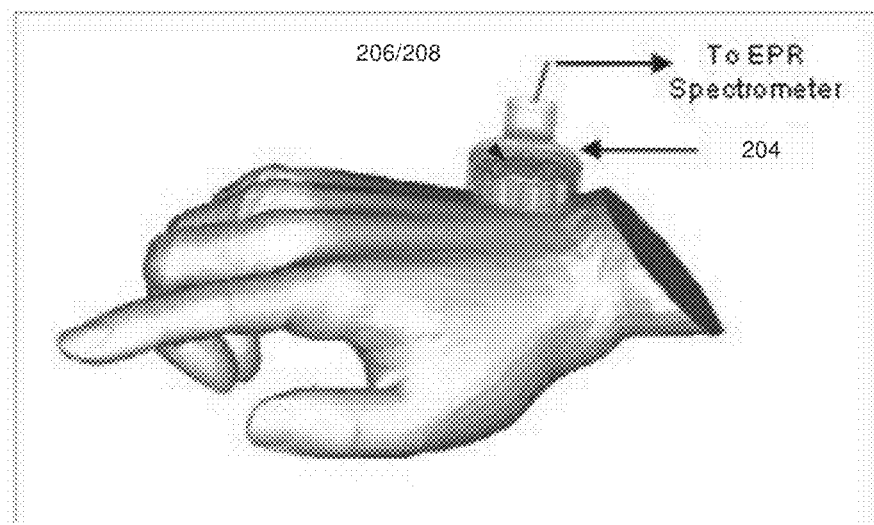

As discussed above, when the magnetic field strength generated by the magnetic assembly 206 is about 86 mT or about 90 mT or about 100 mT, the EPR frequency is about 2.4 GHz. The resonator assembly 208 can be configured to resonate at a predetermined frequency corresponding to the EPR frequency. Alternatively or additionally, an outer dimension 255 of the resonator assembly 208 can optionally be about 8 mm or about 13 mm. The coupling loop 210 electromagnetically couples the resonator assembly 208 to a spectrometer and/or RF source. A wand including the magnet and resonator assembly discussed above can operate in a pulsed mode, with the field inhomogeneity of 1000 ppm or less across the entire region-of-interest. An echo sequence can be used to measure the relaxation times (T2) accurately, which is inversely proportional to the oxygen concentration (pO2), for example, the oxygen concentration of a tissue of a subject. The magnet and resonator assemblies 206, 208 discussed above can be contained in a housing 204 as shown in FIG. 2D. The housing 204 containing the above magnet and resonator assemblies discussed above can have an overall dimension less than 35 mm. In other words, the housing 204 can optionally be a compact, handheld wand.

The results of spin echo simulations for the magnet assembly and resonator assembly discussed above with regard to FIGS. 2A-2D are shown in FIGS. 6A-6B. The results demonstrate that T1=T2=1 μsec, which roughly corresponds to 10 mmHg for Butoxy. The pulse width for both π/2 and π pulse is 3 nsec. Additionally, π/2 pulse occurs at 0.1 μs, π pulse occurs at 0.4 μs, and the echo occurs at 0.7 μs. The median value of the magnetic field (B0) in the region-of-interest was 0.0779 T, therefore the corresponding excitation frequency is 2.18 GHz. The region-of-interest where the EPR probes reside is $-1.0<z<1.0$, $-1.0<y<1.0$, $-7.5<z<-6.5$ mm. The theoretical SNR is 38779.2.

Figure 3A:
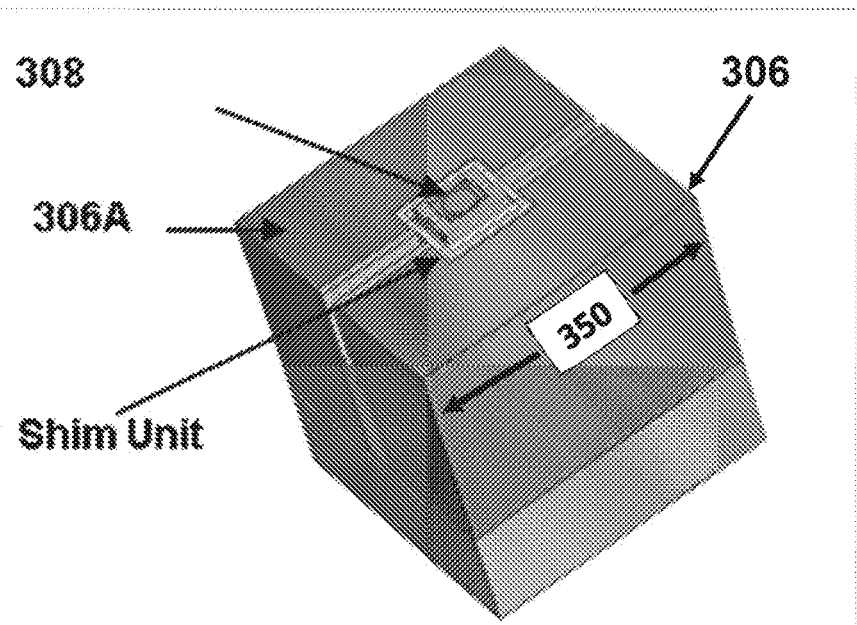
Figure 3B:
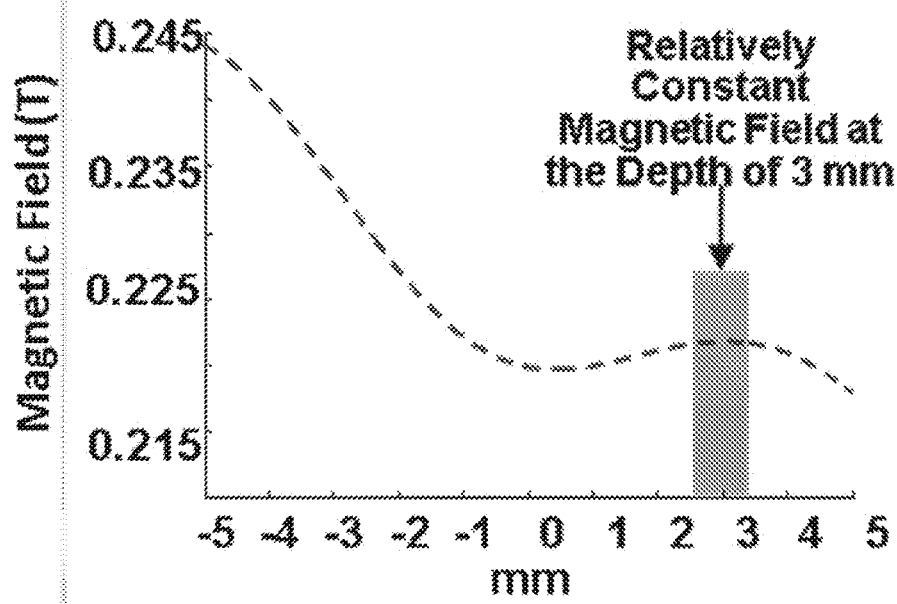

Referring now to FIGS. 3A-B another example magnet and resonator assembly is shown. A magnet assembly 306 can include a plurality of magnets 306A. Additionally, the resonator assembly 308 can be arranged in a space between at least two permanent magnets. Each of the magnets 306A can optionally be a permanent magnet such as a permanent magnet formed from SmCo. Alternatively or additionally, each of the magnets 306A can optionally be a hexahedron. Similar to above, increased flexibility in achieving and adjusting the magnetic field to the desired homogeneity and/or strength is obtained by providing relatively small magnets. Magnet assembly 306 can optionally be used in an SCOM wand, for example. A magnet assembly used in an SCOM wand can differ from the magnet assembly used in a TCOM wand due to the different magnetic field strengths. For example, to generate an adequate, uniform magnetic field in the subcutaneous region which is approximately 3 mm from the magnet assembly 306, a larger magnet assembly can be provided. The magnet assembly 306 can be configured to generate a substantially uniform magnetic field in the region-of-interest, for example, having a field inhomogeneity of approximately 1000 ppm or less across the entire region-of-interest. Alternatively or additionally, the field inhomogeneity can be approximately 900-1000 ppm, 800-900 ppm, 700-800 ppm, 600-700 ppm, 500-600 ppm, 400-500 ppm, 300-400 ppm, 200-300 ppm, 100-200 ppm or less than 100 ppm across the entire region-of-interest. Optionally, the substantially uniform magnetic field can have a strength in the range of approximately 200-220 mT, corresponding to frequency range of from about 1 GHz to about 6.2 GHz, across the entire region-of-interest. For example, the substantially uniform magnetic field can optionally have a strength of 220 mT, corresponding to a frequency of 6.2 GHz, across the entire region-of-interest. This is shown by the graph of FIG. 3B, where the magnetic field strength is approximately 220 mT at approximately 3 mm. The magnetic field has a homogenous "sweet spot" right inside the region-of-interest—located at a distance of approximately 3 mm from the wand surface. When the magnetic field strength generated by the magnetic assembly 306 is approximately 220 mT, the EPR frequency is approximately 6.2 GHz. The resonator assembly 308 can be configured to resonate at a predetermined frequency corresponding to the EPR frequency. Additionally, an outer dimension 350 of the magnet assembly 306 can be approximately 70 mm. Alternatively or additionally, an outer dimension of the resonator can optionally be about 8 mm or about 13 mm. Similar to the housing shown in FIG. 2D, the housing containing the magnet and resonator assemblies discussed with regard to FIGS. 3A-B can have an overall dimension less than 70 mm. In other words, the housing can optionally be a compact, handheld wand.

For transcutaneous monitoring, example operational parameters can be: RF frequency of about 2.4 GHz, resonator Q of about 60 and RF pulses of 20 ns. These example parameters provide a bandwidth of excitation of about 50 MHz, which conforms to the bandwidth of the resonator assembly and also excites all the spins in the region-of-interest for the inhomogeneity of about 5000 ppm. For subcutaneous monitoring, example operational parameters can be: RF frequency of about 6.2 GHz, resonator Q of about 60 and RF pulses of 8 ns. The resulting excitation bandwidth of about 130 MHz conforms to the bandwidth of the resonator assembly and also excites all the spins in the region-of-interest for the inhomogeneity of about 5000 ppm.

Alternatively or additionally, the following options can be used to ensure proper positioning of the oxygen-sensitive EPR probe material and housing. For TCOM wands, a protrusion can be provided on the top surface of the oxygen-sensitive EPR probe material that slides into a corresponding indentation in a distal end of the housing to ensure that the oxygen-sensitive EPR probe material resides in the region-of-interest. For SCOM (or TCOM) wands, proper positioning of the housing with respect to the implanted oxygen-sensitive EPR probe material can be ensured by increasing the magnet size to ensure field homogeneity across a larger region-of-interest, which makes the measurement less susceptible to misalignments between the oxygen-sensitive EPR probe material and the housing. Additionally, marking the implantation location or identifying it using an infrared light source can also assist the precise placement of the housing.

As discussed above, an EPR signal is detected from an oxygen-sensitive EPR probe material. Example oxygen-sensitive EPR probe materials are discussed in U.S. Patent Application Publication No. 2012/0296188 to Kuppusamy et al., published Nov. 22, 2012 and entitled "Devices and Methods for Measuring Oxygen," the disclosure of which is hereby incorporated by reference in its entirety. The EPR probes can be polymer-encapsulated oxygen-sensitive probes. The oxygen-sensitive EPR probe materials can be either implanted into tissue of a subject for subcutaneous measurements (e.g., OxyChips) or adhered to a surface of a tissue of a subject (e.g., the subject's skin) for transcutaneous measurements (e.g., SPOT chips).

In any of the embodiments described herein particularly embodiments in which the EPR probe is embodied as an OxyChip and embodiments in which the EPR probe is embodied as a SPOT chip, the EPR probe preferably includes an oxygen-sensing EPR material.

The oxygen-sensing EPR material of the present embodiments is preferably a paramagnetic material. Representative examples of oxygen-sensing EPR materials suitable for the present embodiments include, without limitation, india ink, coals, char, carbon black, lithium phthalocyanine, lithium naphthalocyanine, nitroxides, and trityl radicals.

In some embodiments of the present invention the oxygen-sensing EPR material comprises radicals of lithium phthalocyanine derivative compounds.

As used herein "litium phthalocyanine derivatives" includes, but is not limited to lithium phthalocyanine (LiPc) derivatives and radicals thereof, lithium naphthalocyanine (LiNc) derivatives and radicals thereof, and lithium anthraphthalocyanine derivatives and radicals thereof.

In some embodiments of the present invention the oxygen-sensing EPR material comprises lithium octa-n-butoxynaphthalocyanine (LiNc-BuO), and in some embodiments of the present invention the oxygen-sensing EPR material is LiNc-BuO.

LiNc-BuO is a derivative of LiPc and LiNc, similar in molecular structure. The advantage of using LiNc-BuO is that it provides a single, relatively sharp and isotropic EPR spectrum characterized by a Lorentzian shape. Another advantage is its relatively high spin density, e.g., compared to LiPc and LiNc. An additional Another advantage is that LiNc-BuO exhibits a linear variation of line-width with changes in oxygen concentration, which linear variation is generally independent of particulate size.

Oxygen levels are expected to stay below 50 mmHg, ensuring that LiNc-BuO (T2 of about 0.11 µs at 50 mmHg) can be used with pulsed spectrometers.

In various exemplary embodiments of the invention the oxygen-sensing EPR material is embedded in an oxygen-permeable material, which is preferably, but not necessarily a polymer. The oxygen-permeable material is preferably biocompatible.

Optionally and preferably the oxygen-sensing EPR material is embedded in the oxygen-permeable material in a particulated form, preferably as micro- or nano-particles, more preferably as micro- or nano-crystalline particles.

Representative examples of oxygen-permeable material suitable for the present embodiments including, without limitation, polydimethylsiloxane (PDMS), an amorphous fluoropolymer, fluorosilicone acrylate, cellulose acetate, polyvinyl acetate, and combinations thereof. In a preferred embodiment the oxygen-permeable material comprises PDMS, and in another preferred embodiment the oxygen-permeable material is PDMS. Although this description specifically sets forth several biocompatible oxygen permeable materials, those of skill in the art will recognize that other biocompatible oxygen permeable materials may be used.

In some embodiments of the present invention the oxygen-sensing EPR material is attachable to the skin of the subject, for example, by means of a sticker attachable to the skin, as illustrated in FIG. 11.

OxyChips can be prepared by doping PDMS with oxygen sensitive microcrystals of LiNc-BuO by the technique of polymerization and cast-molding. For example, liquid silicone injection molding and microinjection molding fabrication methods can be employed for OxyChip development. The fabrication of OxyChip can involve mixing the base and catalyst of medical-grade silastic MDX4-4210 at manufacturer-recommended ratios. The LiNc-BuO oxygen-sensing particulates can be added to one of these components prior to mixing. Upon cooling, the pieces will be removed from the die and set aside. The largest dimension of the resulting chips can be less than 0.5 mm.

Figure 4:
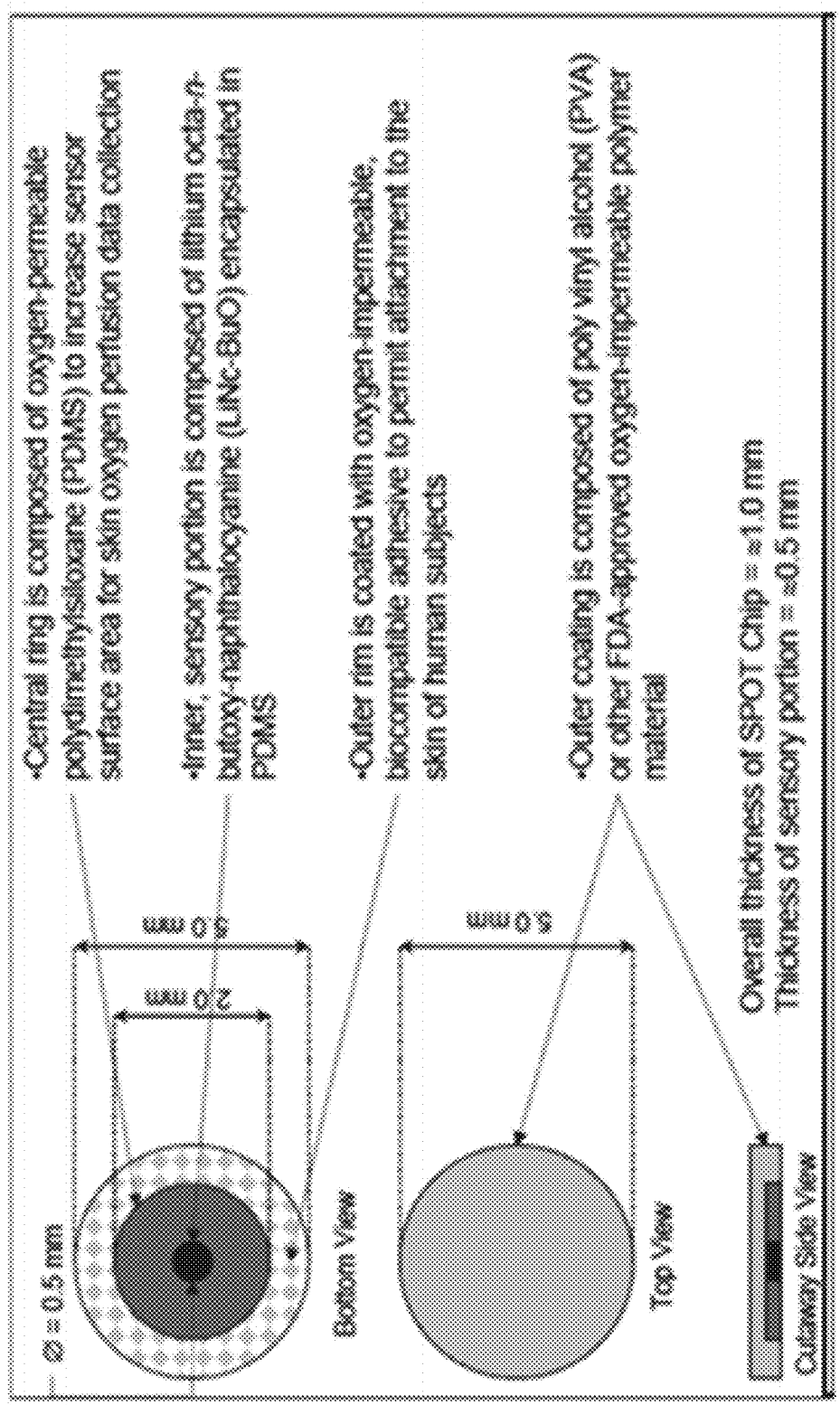

SPOT chips can be extensions of OxyChips. In order to adapt OxyChip for transcutaneous measurements, the OxyChip can be encapsulated with oxygen-impermeable material on all non-tissue-contacting surfaces. Fabrication of the SPOT chip can be accomplished in three steps. The first step in the fabrication of the SPOT chip is similar to the fabrication of OxyChip as described above. The second step involves producing the PDMS ring that surrounds the sensory portion from the first step. The process used to fabricate the sensory portions can be replicated in this step, with one exception. LiNc-BuO crystal is not added to the process during the injection molding of this ring—only pure polymer will be used. Upon cooling, the pieces can be removed from the die and set aside. The third step of the process can be to coat all but the basal surface with a 120 microns thick oxygen impermeable layer of parylene (PDX-C). An example SPOT chip is shown in FIG. 4. For example, an outer ring of oxygen-permeable PDMS 402, oxygen sensitive microcrystal of LiNc-BuO 404 and an oxygen—impermeable outer layer 406 are shown.

A full characterization following fabrication can be performed to ensure the OxyChips and/or SPOT chips are performing as expected. The oxygen responsivity of the chips can be evaluated using X-Band (9.8 GHz) as well as L-band (1.2 GHz) EPR spectroscopy by exposing chips to various combination of oxygen and nitrogen. Total amount of LiNc-BuO in the chip controls the SNR. To maintain a constant SNR across different chips, the amount of LiNc-BuO in each chip can be computed by comparing the EPR signal intensity. The completeness and integrity of the polymer layers can be established by analyzing the surface features and morphology using atomic force microscopy (AFM) and scanning electron microscopy (SEM). Special SPOT chips can be developed where all the chip surfaces are coated with parylene. Full encapsulation can take place under a nitrogen (anoxic) environment. If the parylene layer is oxygen impermeable, subsequent EPR spectrometry tests at X-Band (9.8 GHz) should produce an anoxic line width. Tests to determine whether or not the units can be sterilized to ensure safety of the human subjects can be performed. Autoclaving and irradiation with ultraviolet light can be used to sterilize the chips.

Figure 5A:
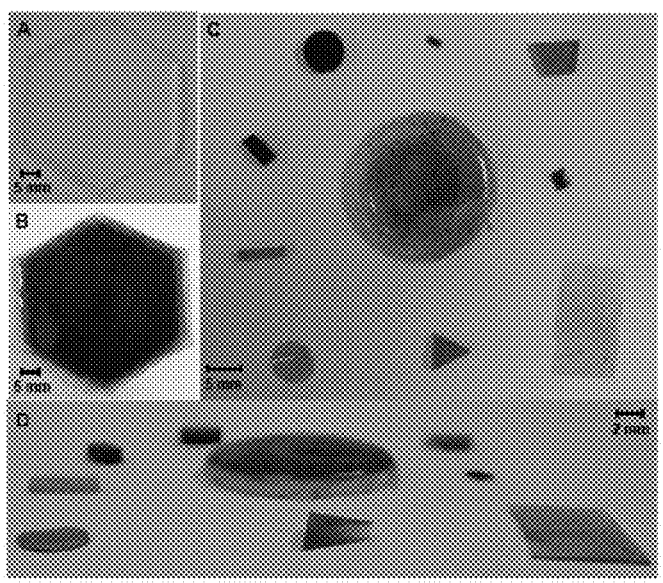
Figure 5B:
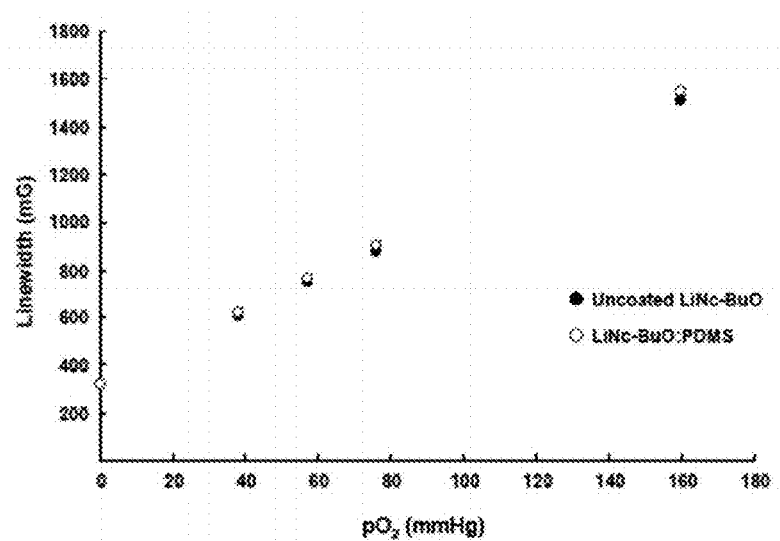
Figure 5C:
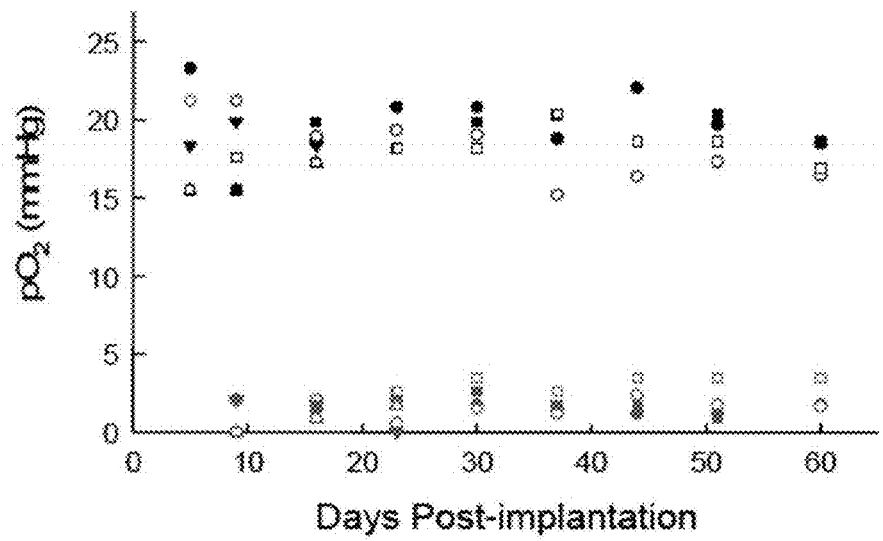

Referring to FIG. 5A, example oxygen-sensitive EPR probe materials are shown. In particular, OxyChips fabricated by cast molding and polymerization, by dispersing the LiNc-BuO crystals in the uncured polymer base catalyst mixture and curing at 75° C. for 7 hours are shown. The color of the chip indicates the relative amount of LiNc-BuO. Referring now to FIGS. 5B-5C, data regarding example oxygen-sensitive EPR probe materials are shown. In FIG. 5B, the effect of molecular oxygen (pO2) on the EPR line width of an OxyChip is illustrated. The oxygen response of OxyChip was linear over the range of pO2 employed (0 to 160 mmHg). The response was very similar to the response exhibited by unencapsulated LiNc-BuO crystals. In FIG. 5C, the results of a stability test for an OxyChip in vivo is shown. The oxygen-response of the OxyChip implanted in the leg muscle of C3H mice was monitored up to 60 days using a conventional EPR spectrometer.

Methods for measuring transcutaneous and/or subcutaneous oxygen concentration of a tissue of a subject are provided herein. The subject can be any mammal, human or non-human. As discussed above, oxygen concentration of tissue can be determined by measuring the relaxation times (T2) of an oxygen-sensitive EPR probe material. An example method for detecting an electron paramagnetic resonance (EPR) signal from an oxygen-sensitive EPR probe material using a wand and a spectrometer is described below. The wand and spectrometer can be any of the wands and spectrometers discussed above. The method can include detecting a signal in the region-of-interest when a distal end of a housing of the wand is positioned proximal to the oxygen-sensitive EPR probe material, communicating the detected signal through the coupling loop to the spectrometer and processing the received signal to measure EPR resonance of the EPR probe.

As used herein the term "about" or "approximately" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

A probe with reduced dimensions and improved static magnetic field homogeneity was designed.

The magnetic material of the magnet assembly 206 was Samarium cobalt (EEC2:17-31), with maximal energy product of 31 MGOe. The magnet assembly 206 included two parts 206A and 206B each shaped as a half of a cylinder as illustrated in FIG. 7. The parts 206A and 206B were positioned opposite to each other in a non-contact arrangement characterized by a cylindrical symmetry to form a generally cylindrical shape with non-magnetic or paramagnetic gaps separating between the surfaces of the parts 206A and 206B. The two cylinder halves were separated by 3 mm gap. The outer diameter Do of the generally cylindrical shape was 20.6 mm, the inner diameter Di was 16 mm, and the axial length h was 12 mm. The magnetization M of the first and second parts was parallel and anti-parallel to the symmetry axis of the cylinder, respectively. The magnet assembly 206 was assembled by means of a non-conductive and non-magnetic spacer 510 (FIG. 10), which in this example was made of plastic.

The direction of magnetization was selected to form close to the edge of magnet assembly 206 a region in which the magnetic field is generally a homogeneous. Homogeneous magnetic field close to the edge is advantageous since the oxygen-sensing EPR material (for example, the sticker attached to the skin) is positioned at this region.

A 2D cut showing the magnetic field contour is shown in FIG. 8. As shown, there is a homogenous region (with a deviation of 1-2 G/mm) at the surface of the magnet structure, with field of about 100 mT.

The resonator assembly 208 was a loop-gap resonator assembly, made of copper. The resonator assembly was designed to allow the sticker with paramagnetic material to fit inside the resonator. A schematic illustration of the resonator assembly is illustrated in FIGS. 9A (perspective view) and 9B (cross-sectional view), showing the resonator assembly 208 and gap 502. The outer diameter of the resonator was 7.8 mm and the inner diameter of the resonator was Di=2 mm. An additional opening was formed at the gap region as shown at 512. The diameter of opening 512 was 1 mm.

The gap 502 was partially filled with a patch of a Rogers RT/6010 (dielectric constant 10.2) laminate, 5 mm in thickness in order to adjust the resonant frequency of the resonator assembly to a frequency of about 2.5 GHz, based on the static field of the magnet. A Sapphire tuning element, Temex Ceramics AT 6933-1 SL, was inserted into opening 512 for further fine tuning of the resonant frequency.

The resonator assembly 208 included a resonator support element 504 made of "Rexolite®". The resonator support element 504 was in the form of a circular cylindrical retainer which encircled the resonator body 506. The outer diameter of resonator support element 504 was 12 mm and the inner diameter of resonator support element 504 was 7.8 mm.

The resonator was designed to function as an independent unit, to allow the resonator to operate independently using a static magnetic field source other than the magnet shown in FIG. 7.

The resonator support element 504 was fitted into the interior volume of the magnet assembly 206 by means of a shield 508, which in this example was made of brass. A perspective view of the overall arrangement, including the magnet assembly 206, resonator assembly 208, the shield 508, the spacer 510 and the RF coupling loop 110, is illustrated in FIG. 10.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for detecting an electron paramagnetic resonance (EPR) signal from an oxygen-sensitive EPR probe material, comprising:

a spectrometer having a radio frequency (RF) source and being configured for generating, via said RF source, an RF pulse sequence selected for measurement of T2 relaxation times; and a housing containing a magnetic assembly, a resonator assembly and a coupling loop, wherein the magnet assembly is configured to apply a magnetic field to a region-of-interest comprising the EPR probe and wherein the resonator assembly is in operative communication with the RF source through the coupling loop and is configured to resonate at a predetermined radio frequency, the housing having a distal end positionable proximal to the EPR probe;

said spectrometer being in operative communication with the resonator assembly through the coupling loop, wherein the spectrometer is configured to receive a signal from the coupling loop and to process the received signal to measure said T2 relaxation times.

2. The system of claim 1, wherein the EPR probe comprises an oxygen-sensitive EPR material embedded in an oxygen-permeable polymer.

3. The system of claim 2, wherein the EPR probe is adherable to a surface of a tissue of a subject.

4. The system of claim 3, wherein the spectrometer is further configured to obtain data corresponding to a transcutaneous oxygen concentration of the tissue from the signal.

5. The system of claim 3, wherein the distal end of the housing includes an indentation for accommodating a portion of the EPR probe.

6. The system of claim 1, wherein the EPR probe is implanted in a tissue of a subject.

7. The system of claim 6, wherein the spectrometer is further configured to obtain data corresponding to a subcutaneous oxygen concentration of the tissue from the signal.

8. The system of claim 1, wherein the housing is a handheld wand.

9. The system of claim 8, wherein the region-of-interest is located at least partially external to the handheld wand.

10. The system of claim 8, wherein the region-of-interest is located entirely external to the handheld wand.

11. The system of claim 10, wherein the region-of-interest is located approximately 3 mm from the handheld wand.

12. The system of claim 1, wherein a maximum size of the region-of-interest is approximately 0.5 mm×0.5 mm×0.5 mm.

13. The system of claim 1, wherein the magnetic assembly comprises a plurality of magnets, the magnets being arranged around the resonator assembly.

14. The system of claim 13, wherein the magnets are arranged in a ring around the resonator assembly.

15. The system of claim 1, wherein the magnet assembly is configured to generate a substantially uniform magnetic field in the region-of-interest.

16. The system of claim 15, wherein the substantially uniform magnetic field has a field inhomogeneity of approximately 1000 ppm or less across the entire region-of-interest.

17. The system of claim 16, wherein the predetermined radio frequency is substantially greater than 250 MHz.

18. The system of claim 17, wherein the predetermined radio frequency is in a range between approximately 2.0 GHz and 6.2 GHz.

19. The system of claim 18, wherein the substantially uniform magnetic field has a strength of approximately 60-150 mT.

20. The system of claim 18, wherein the substantially uniform magnetic field has a strength of approximately 200-220 mT.

21. The system of claim 1, wherein the resonator assembly is a loop-gap resonator.

22. The system of claim 1, wherein the magnet assembly comprises a plurality of permanent magnets each having a shape of a portion of a cylindrical sector.

23. The system of claim 1, wherein the magnet assembly comprises a first permanent magnet and a second permanent magnet each having a shape of half of a cylinder.

24. A wand system for use with a system for detecting an electron paramagnetic resonance (EPR) signal from an oxygen-sensitive EPR probe material, comprising:
a housing containing a magnetic assembly and a resonator assembly, wherein the magnet assembly is configured to apply a magnetic field to a region-of-interest comprising the EPR probe material and wherein the resonator assembly comprises a loop-gap resonator configured to resonate at a predetermined radio frequency, the housing having a distal end positionable proximal to the EPR probe material.

25. A method for detecting an electron paramagnetic resonance (EPR) signal from an oxygen-sensitive EPR probe material using a wand and a spectrometer, the wand including:
a housing containing a magnetic assembly, a resonator assembly having a loop-gap resonator and a coupling loop, wherein the magnet assembly is configured to apply a magnetic field to a region-of-interest comprising the EPR probe and wherein the loop-gap resonator is configured to resonate at a predetermined radio frequency, the method comprising:
generating an RF pulse sequence selected for measurement of T2 relaxation times;
detecting a signal in the region-of-interest when a distal end of the housing of the wand is positioned proximal to the EPR probe;
communicating the detected signal through the coupling loop to the spectrometer; and
processing the received signal to measure said T2 relaxation time.

* * * * *